United States Patent [19]

Prokoski et al.

[11] Patent Number: 5,163,094
[45] Date of Patent: Nov. 10, 1992

[54] METHOD FOR IDENTIFYING INDIVIDUALS FROM ANALYSIS OF ELEMENTAL SHAPES DERIVED FROM BIOSENSOR DATA

[75] Inventors: Francine J. Prokoski, 1510 Inlet Ct., Reston, Va. 22090; Jeffrey S. Coffin, Sterling, Va.; Robert B. Riedel, Great Falls, Va.

[73] Assignee: Francine J. Prokoski, Reston, Va.

[21] Appl. No.: 672,320

[22] Filed: Mar. 20, 1991

[51] Int. Cl.$^5$ .............................................. G06K 9/00
[52] U.S. Cl. ........................................ 382/2; 382/1; 358/113; 250/334
[58] Field of Search .............................. 382/2, 1, 8, 6; 358/113; 250/334

[56] References Cited

U.S. PATENT DOCUMENTS

| | | |
|---|---|---|
| 3,611,290 | 10/1971 | Luisi . |
| 3,805,238 | 4/1974 | Rothfjell . |
| 4,135,147 | 1/1979 | Riganati et al. . |
| 4,300,160 | 11/1981 | Pusch et al. . |
| 4,525,859 | 6/1985 | Bowles et al. . |
| 4,646,352 | 2/1987 | Asai et al. . |
| 4,699,149 | 10/1987 | Rice . |
| 4,858,000 | 8/1989 | Lu . |
| 4,975,969 | 12/1990 | Tal . |

OTHER PUBLICATIONS

Prokoski, Francine J., Disguise Detection and Identification Using Infrared Imagery; Proceedings of SPIE, vol. 339, May 1982.

*Primary Examiner*—Jose L. Couso
*Attorney, Agent, or Firm*—Laubscher & Laubscher

[57] ABSTRACT

A method and apparatus for identifying individuals is characterized by the analysis of elemental shapes derived from biosensor data presented in n dimensions, particularly facial thermograms. A thermal image of the individual's face is generated in accordance with the thermal energy patterns thereof. The thermal image is converted to a digital representation comprising a matrix of pixels, the intensity of each pixel corresponding with the level of thermal energy of a corresponding portion of the image. The digital representation of the image is normalized for size and equalized to a standard histogram to produce an image containing elemental shapes comprising contours corresponding with unique structural features of the individual.

14 Claims, 8 Drawing Sheets

Entry Station Flow Diagram

FIG. 11

METHOD FOR IDENTIFYING INDIVIDUALS FROM ANALYSIS OF ELEMENTAL SHAPES DERIVED FROM BIOSENSOR DATA

BACKGROUND OF THE INVENTION

The problem of ascertaining the identity of an individual or verifying whether an individual is the person he claims to be is a common one continually faced by individuals, businesses, and governments. Methods for positive identification of an individual usually include reliance upon knowledge of restricted information (such as a password), possession of a restricted article (such as a passkey), or physical appearance (such as matching a reference photo).

Security based upon knowledge or possession may be compromised without discovery since the information or article may be extorted from its rightful owner. The third methodology, commonly referred to as biometric techniques, is considered less vulnerable to mistaken identity. The best known biometric technique and the one considered most secure is fingerprint analysis. However, other biometric techniques exist. The present invention relates to an identification technique utilizing thermal imaging.

Skin temperature is a result of the balance between the heat flow from tissue to the skin surface and the heat flow from the surface to the surroundings. The basic mechanisms for transport of heat from the tissues to the skin surface include conduction throughout the tissues and convection by the flow of blood from the warm arterial supply through the capillary bed into the venous plexus. Metabolic heat generation is a second order influence compared to the convection transport mechanism of the blood perfusion. Thus in the absence of active superficial veins, the diffuse avascular skin temperature is directly related to the blood perfusion per unit volume of tissue, including the skin itself as well as tissues approximately 2 to 3 cm deep to the skin. Active superficial veins are also a possible indicator of regional blood flow. These are demonstrated as well-defined patterns of increased skin temperature. Skin temperature immediately overlying the vein is only a few tenths of a degree Celsius lower than the temperature of the blood flowing in the vein itself.

A variation of 3.5 degrees Fahrenheit is usual across a human facial surface. In the case of severe medical abnormalities, or when the ambient temperature is severe, the range may be twice as large, and its average value may vary. The heat energy given off by the face is changed to electrical energy and greatly amplified by the electronic circuitry of a thermal imaging system. Following amplification, the electrical energy is digitized. A facial "thermogram" is the resultant two-dimensional image obtained by scanning each section of the face onto one or more detectors which are sensitive in the infrared range. The most commonly used medical thermal imagers produce an image which comprises approximately 60,000 individual heat recordings. Most commonly used scanning infrared cameras do not accurately measure vein temperature because the modulation transfer function of the optics of these cameras produces a measurement that is related to the average temperature over almost 1 cm$^2$ of scanning surface. Thus the size of the vein will influence the indicated temperature.

Because a thermograph operates at a distance from the subject and detects and records only radiant heat spontaneously emitted from the body surface, it constitutes a painless, non-invasive, passive method of recording body surface temperatures. In general, the nose, cheeks, ears, and the avascular corneas of the eyes are cool, as are the hair-insulated eyebrow, eyelash, and scalp regions. The anterior portion of the forehead is warm and has a narrow range of temperature variation over its surface. Heat is normally trapped by skin folds, at the canthi and along the free margins of the eyelids. Essentially symmetrical facial thermograms are found almost without exception in healthy subjects.

In accordance with the present invention, facial thermograms are processed to extract elemental shapes therefrom. The elemental shapes—like a fingerprint—are unique to an individual. Thus, the identity of an individual may be ascertained by comparing current elemental shapes with those from a reference.

BRIEF DESCRIPTION OF THE PRIOR ART

Individuals identify one another primarily by recognizing their faces. It is therefore understandable that systems would be developed which would attempt to replicate how persons recognize one another. Various patents have been issued which utilize known photographic or other visual images for comparison with unknown images in order to automate the recognition task. In the facial curve method of the Rothfjell U.S. Pat. No. 3,805,238, facial curves (two or three dimensional) of an individual taken from fullface, forty-five degree angle, and profile (ninety degree angle) are stored on an identity card or in a data processing machine. Identification of the individual is performed by first visually comparing the photographs on the identity card to the individual presenting the card and then taking an image of the individual and automatically comparing by computer the curves stored on the identity card with curves derived from the image. In order to properly compare such an image with the computer data, however, the individual must be positioned and aligned in front of a glass screen.

It is also known in the art to measure facial features utilizing ratios obtained from a set of measurements taken from a facial image as disclosed in the Tal U.S. Pat. No. 4,975,969. The use of binary images obtained by thresholding facial images collected under relatively uncontrolled conditions and finding the best match among small groups of known individuals is disclosed to Lu in the U.S. Pat. No. 4,858,000.

The time required for enrollment and verification, the difficulty in automating the techniques, and variabilities resulting from lighting conditions and shadows are major limitations to the routine, unattended use of these and other facial recognition systems which utilize photographs or video images. In addition, such systems are vulnerable to forgery through disguise and use of photographs or mannequins.

Identification techniques utilizing infrared thermal imaging are known in the art as evidenced by the Rice U.S. Pat. No. 4,699,149. This patent is predicated upon the discovery that the arrangement of veins in a local portion of an individual's body is a unique characteristic of that individual. Identification is performed by linearly scanning a region of skin at the wrist and detecting the position of subcutaneous blood vessels by measuring a parameter such as the reflection of incident radiation. A transducer is constrained to follow a particular path, and the resulting linear scan measurements are thresholded to produce a binary image which constitutes the identification signature. The measured signature and predetermined signature at the same location are compared.

A number of drawbacks are inherent in the Rice system. For example, active illumination or heating of the area being scanned is required, as is identical replication of the small skin area selected for scanning. These requirements may cause discomfort to the individual. Moreover, identification can not be verified from a distance as is necessary for security access systems.

The present invention was developed in order to overcome these and other drawbacks of the prior identification techniques by providing a passive identification method wherein unique elemental shapes are extracted from a thermal image of the individual.

SUMMARY OF THE INVENTION

Accordingly, it is a primary object of the present invention to provide a method for identifying individuals from biosensor data. A thermal image of a portion of the individual's body is generated in accordance with the thermal energy patterns thereof. The thermal image is processed to produce a digital representation thereof. The digital representation includes a matrix of pixels and the intensity of each pixel corresponds with the level of thermal energy of a corresponding portion of the image. The digital image is normalized in order to eliminate variables and produce an image containing elemental shapes comprising contours corresponding with unique structural features of the individual. Normalization is accomplished by cropping the image to an area of maximum uniqueness, such as the eye and nose area of the individual's face, standardizing the image for size, and equalizing the image to a standard histogram. The processed image is stored for subsequent identification of the individual.

According to another object of the invention, a region of the image containing specific elemental shapes of interest is defined by geometry, mathematics, or as a bit-map replica of the region in order to provide a signature of the individual.

Correlation techniques are used to compare a previously defined reference signature of an individual with a currently defined signature to confirm the individual's identity.

BRIEF DESCRIPTION OF THE FIGURES

Other objects and advantages of the invention will become apparent from a study of the following specification when viewed in the light of the accompanying drawing, in which.

DETAILED DESCRIPTION

The invention relates to a method and apparatus for uniquely identifying individuals through analysis of elemental shapes derived from biosensor data presented in n dimensions.

In order to confirm the identify of an individual, a reference identification for that individual must be obtained. This is performed by enrolling or storing a thermogram image of the individual in a storage device such as a storage card or a memory for subsequent comparison. In this manner, when the individual presents himself for identification, such as when he desires to gain entry to a secure area, the current thermogram image of the individual can be compared with the stored reference to confirm the individuals's identity. The apparatus for generating a thermogram image of the individual will be described with reference to FIG. 1.

Figures 1, 9:
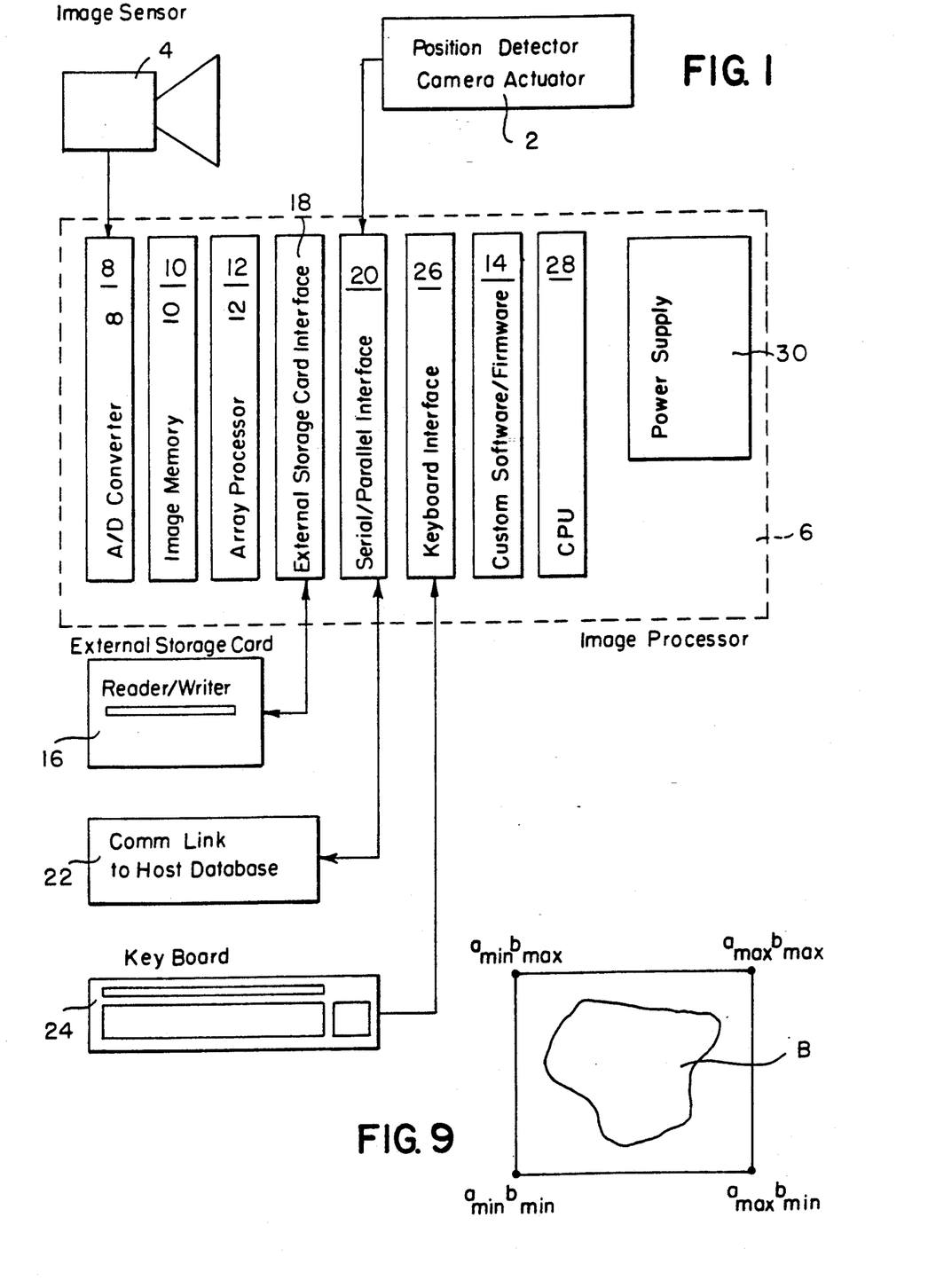
FIG. 1 is a block diagram of the apparatus used to create an identification signature of an individual.
FIG. 9 is a detailed illustration of an elemental shape.

A position detector 2 is used to determine whether the individual is properly framed in front of an image sensor 4. In the preferred embodiment, the face of the individual is that portion positioned in front of the sensor from which the thermogram is generated. As used herein the term face includes all portions of the head imaged by the sensor 4. The degrees of tilt, twist, and tip can be made with reference to polar coordinates establishing the "faceball" as will be described below. The preferred embodiment results in a standard 30° upwards angle to the face during imaging, which reduces the possibility of impinging hair or clothing on the minimum portion of the face required for most accurate identification, that portion being the swath occurring between the approximately horizontal lines established by the uppermost points of the eyebrows and by the nostrils or lowest portion of the nose.

The image sensor 4 preferably comprises a platinum silicide staring array camera although a variety of other infrared imagers of either the array or scanning type may be used. Furthermore, other types on n-dimensional biometric sensors may be used including for example magnetic resonance imagers, digital angiographs, computed tomographs, sonographs, radioisotope imagers, and X-ray devices. Infrared imagers producing emissions in the 3–6 or 8–14 micron ranges are preferred since thermal data from the individual may be collected passively and instantaneously with no risk to the individual.

The camera 4 produces an analog image of the individual's face wherein the intensity level is directly proportional to the absolute temperatures at different points across the face, where the size of the points depends on the imager used.

The analog image is sent to an image processor 6 for analysis. The processor includes an A/D converter 8 which contains a frame grabber circuit to capture the analog image being produced and convert it into a digital format for analysis. Of course, where imaging sensors producing a digital image output are used, there is no need for an additional A/D converter in the processor. The digitized image is stored temporarily in an image memory 10.

An array processor 12 utilizes a RISC co-processor for accelerated processing of algorithms on array type data files. Custom software and firmware 14 contains the routines for applying algorithms to the raw digital image to extract specific data for analysis and comparison as will be described in greater detail below. Logging and control functions are also performed by the software.

An external storage and reader/writer 16 is connected with the image processor 6 via an interface 18. The reader/writer is used to write and read digital information from a card or disk medium containing specific information such as a signature or feature of the image being processed or compared.

A serial/parallel interface 20 is used to provide an input and output between the position detector, camera actuator, and other types of access control apparatus such as a communication link to a host database 22. The link is used to establish communication between the image processor and a host computer for data base interrogation, statistic logging, and other administrative functions.

A keyboard 24 and keyboard interface 26 are used to input manual information to be stored and used with the image information. The keyboard is also used to communicate with the overall system for diagnostics.

The CPU 28 handles the input/output, housekeeping and communication functions. Most of the algorithm routines are handled by the array processor. Finally, a power supply 30 is provided to power the image processor 6.

Figure 2:
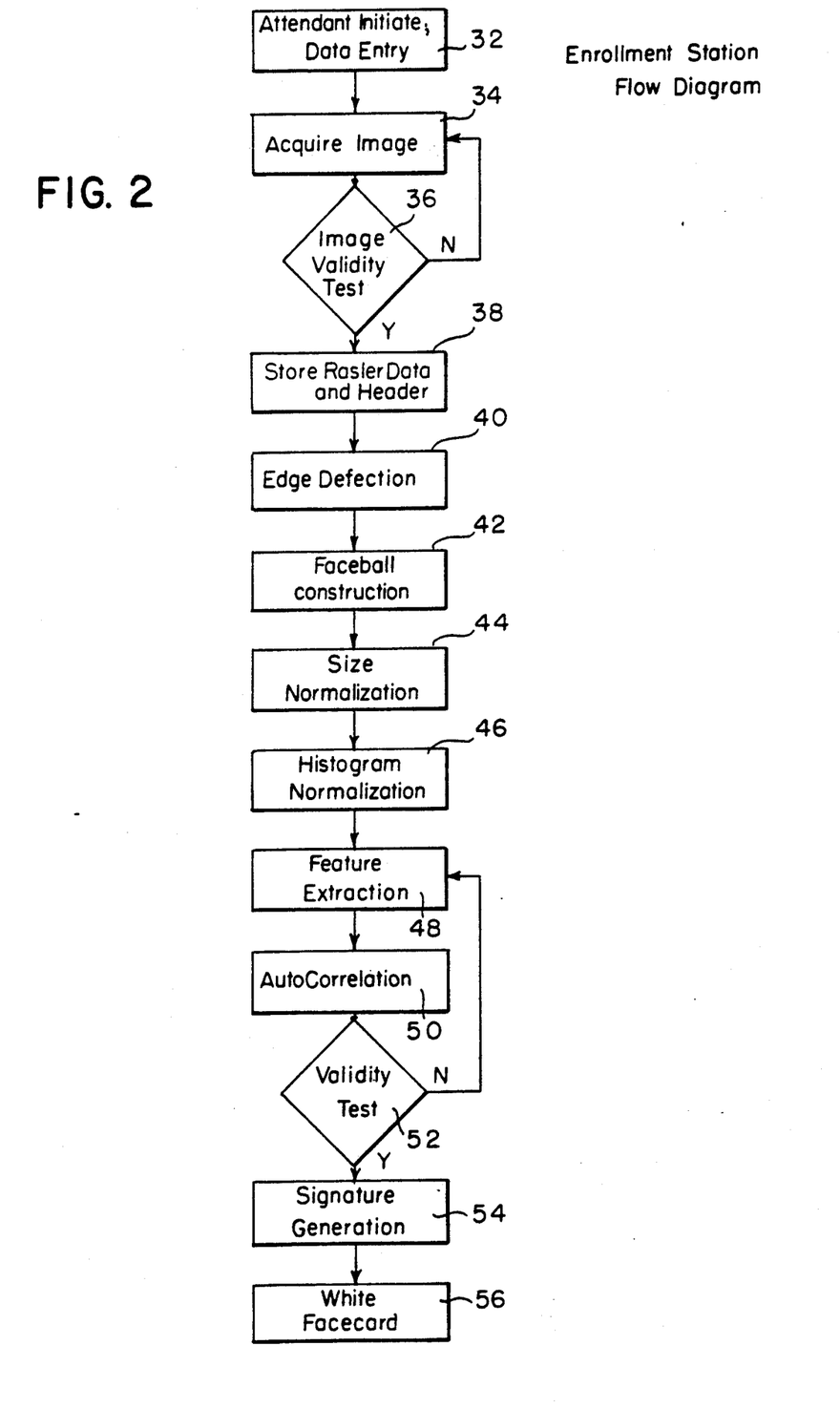
FIG. 2 is a flow chart illustrating the steps for creating the identification signature of an individual from biosensor data in accordance with the invention.

The enrollment process will be described with reference to FIG. 2. The individual to be enrolled removes his glasses, if any, since glass distorts the thermal image, and looks into the reflective surface of the imaging sensor. To obtain a valid image, it is important that the subject be centered within the image frame.

Figure 4:
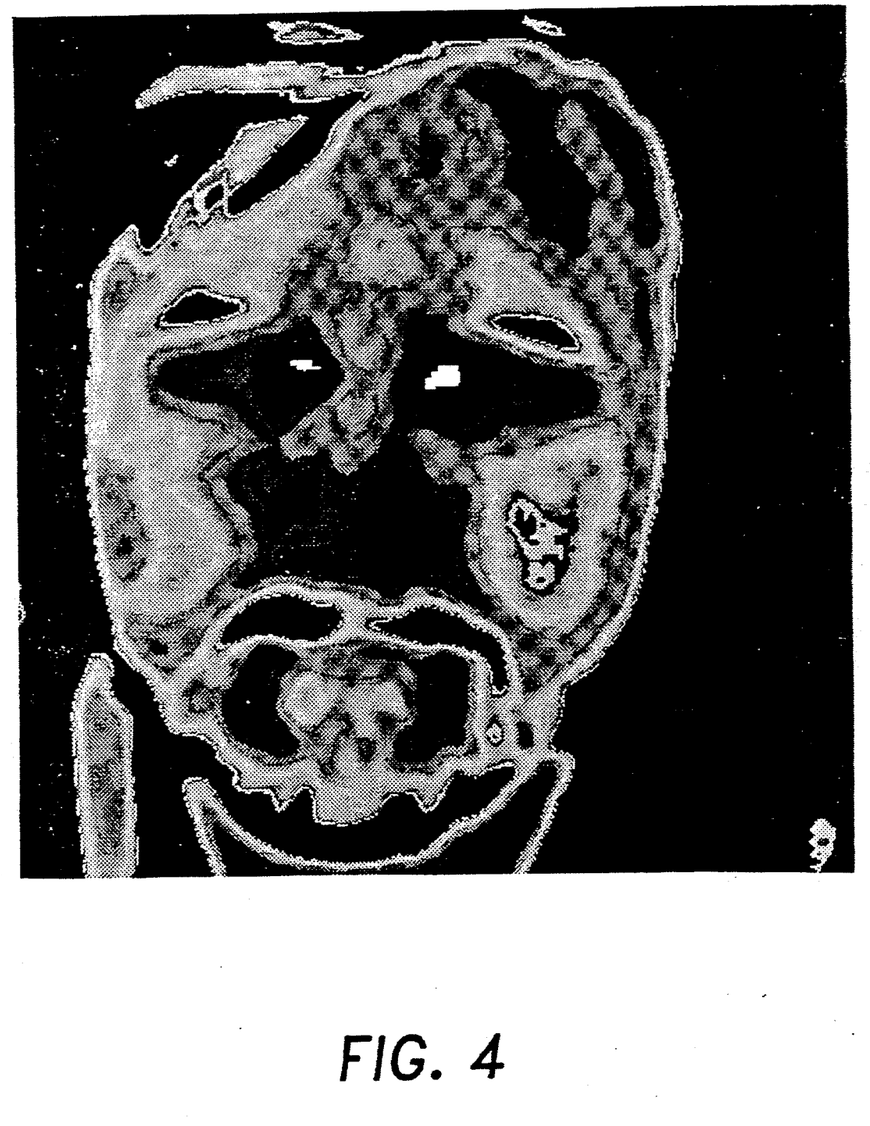
FIG. 4 is a digitized thermal image of an individual's face.

The attendant then initiates data entry 32 by activating the imaging sensor to acquire an analog thermal image 34 of the subject's face in accordance with the thermal energy patterns thereof. The image is tested for validity and clarity 36 and if insufficient, a substitute analog image is generated. An example of an analog thermal image of an individual is shown in FIG. 4.

Figure 5:
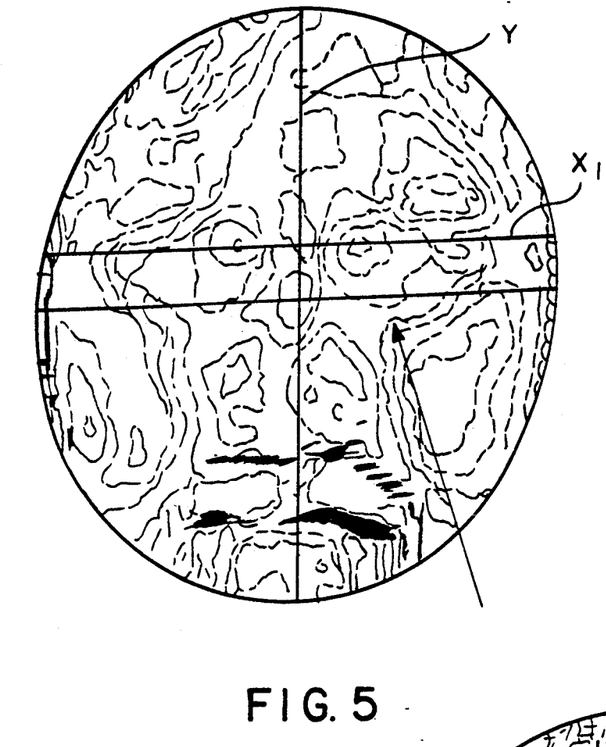
FIG. 5 is the image of FIG. 4 including axes used for cropping.

The thermal image is converted into a digital format, a sample of which is shown in FIG. 5. The digital representation is essentially a matrix or array of pixels. The intensity of each pixel corresponds with the level of thermal energy of a corresponding portion of the analog thermal image. The digital raster data is stored 38 for subsequent normalization and feature extraction.

From the digital representation of the image, the edge of the face is detected 40 using conventional edge detection techniques. Next, a vertical axis Y is created by locating a line through the centers of symmetry of four horizontal scan lines located in the center thirty percent of the image. A secondary horizontal axis $X_1$ is created by constructing a line through the approximate center of the two hottest areas (i.e. those areas of greatest intensity), one on either side of the nose bridge near the sinuses. This line is adjusted to be perpendicular to the vertical axis Y. Next, a primary horizontal axis $X_2$ is generated by creating a horizontal line parallel to the secondary horizontal axis and offsetting the line down by a predetermined percent of the pixel count of the horizontal axis.

A portion of the image—referred to as a faceball—is constructed 42 by forming the largest circle totally within the facial area. In general, there is only one center position for the largest circle. If more than one center position is located, then the most central position will be used as determined by comparing symmetrical features of the thermal signatures of the sinuses and cheeks of the individual. Once the faceball boundary is defined, all data outside the boundary is discarded to produce a non-normalized faceball.

Figure 6:
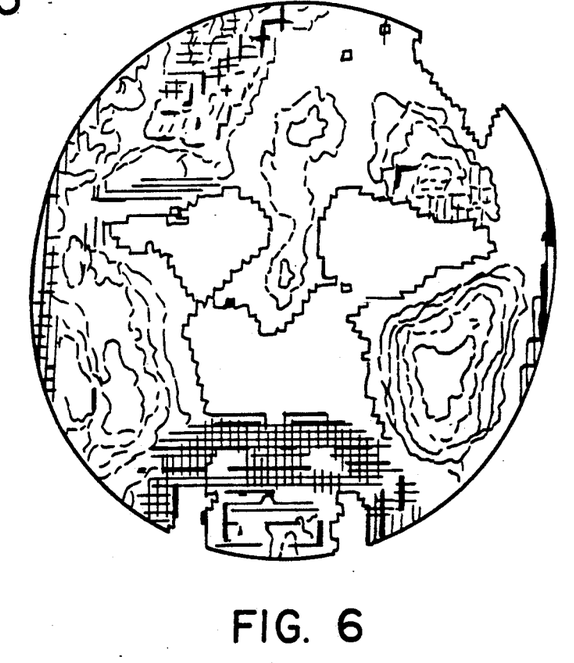
FIG. 6 is a digitized thermal contour image of the image of FIG. 4 after normalization for size.
Figure 7:
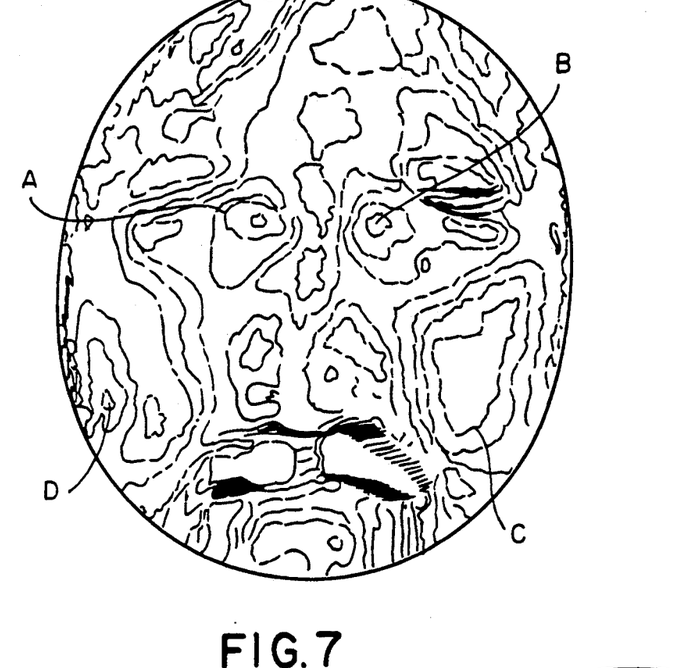
FIG. 7 is the image of FIG. 6 following histogram equalization.

The faceball is normalized for size 44 via measuring and scaling using bilinear interpolation in order to create a standard size (FIG. 6). The image is next scanned for minimum and maximum levels over a predetermined rectangle encompassing features of the eye region, nose region and cheek region containing the elemental shapes. These measurements are used to generate a specific equalization correction transformation (feature enhancement) to achieve a standard histogram 46. This transformation is then applied to all the data in the faceball to create a new equalized faceball as shown in FIG. 7. The normalized faceball may be stored in a database and/or on an identification card.

Analysis of the normalized faceball is performed by feature extraction 48 wherein elemental shapes of the hottest and coldest thermal contours corresponding to the sinuses, cheeks, and nose are identified. Elemental shapes A, B, C, and D are shown in the image of FIG. 7.

An elemental shape is a contour in n-space, the shape of which is related to the extent, intensity, and duration of output from a biosensor as represented by an n-dimensional image. An elemental shape is the smallest replica of nested concentric contours centered at a position or location of interest. The location and contour of the elemental shape of an individual is constant and is determined by the physiological features detected by the biosensor. The size of the elemental shape represented in the image grows or shrinks as a function parameters associated with the biosensor, procedures for or its use, and the imaging system. These parameters included:

a. sensitivity of the biosensor;
    b. threshold settings for image intensity levels;
    c. distance between sensor and subject;
    d. resolution or spot size of the biosensor;
    e. blurring and damping effects of overlaying tissue;
    f. repositioning movements during imaging;
    g. intervening transducers and gels;
    h. artifacts introduced by the imaging and display systems;
    i. dynamic changes in the physiological system during imaging; and
    j. changes introduced by testing and treatment regimens.

The locations of interest depend upon the objective and the biosensor. In the case of thermal imaging for identification, the primary elemental shapes are located in the areas of the sinuses, the cheeks, and the nose. The elemental shape may be used as a fractal to perform compression of the data from the biosensor. By selecting elemental shapes located at areas of greatest concern, image compression may be performed with negligible risk that the most essential information will be lost through compression and decompression. Furthermore, the elemental shape may be used to search a database of compressed images in order to locate a match between known and unknown subjects; to identify changes from time to time in a known subject; or to search for a known condition occurring among subjects.

Through feature extraction of a normalized faceball, a signature of the individual may be defined and stored. Three different techniques may be used for feature extraction.

The preferred technique of feature extraction is to replicate bit maps of geometric areas known to contain the elemental shapes. Since the five areas containing features have been identified, they can simply be cut out based upon a standard set of templates. These mapped areas are extracted along with information of where they were taken from on the original faceball and subsequently stored for later comparison.

A second technique is geometric analysis wherein elemental shapes are identified and mapped as a shape vector table and stored with the location of its centroid in the original faceball.

Finally, mathematical analysis of fractals may be used. In this technique, a specific elemental shape is identified and stored as a fractal representation along with information relating to its location in the original faceball.

Regardless of the feature extraction technique, the extracted date file is autocorrelated 50 and tested for validity 52 for accurate signature generation 54 of the individual. The data is then stored in a storage device or written on a facecard 56 to provide a permanent signature record.

The present invention is particularly suited for use in connection with security area access or entry protection through a recognition of authorized individuals. Use of the invention for authorized access to a secure area will be described with reference to FIG. 3.

Figure 3:
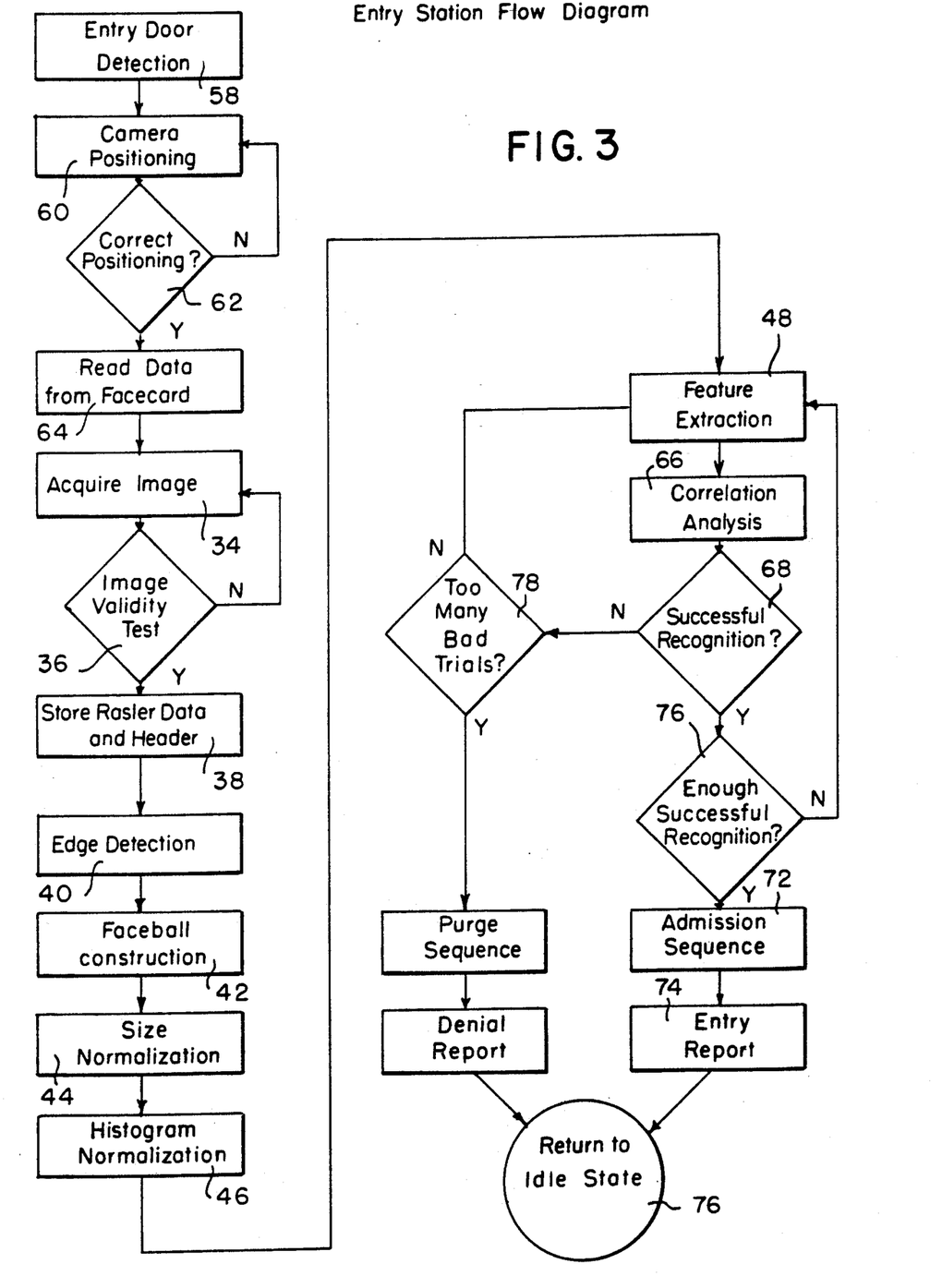
FIG. 3 is a flow chart illustrating the steps for identifying an individual to ascertain whether entry of the individual to a secure area is to be provided.

An individual seeking access through a controlled checkpoint is detected at the entry door 58. The individual positions himself relative to an image sensor camera 60 and the positioning is checked 62 so that a full view of the face of the individual is obtained. The subject inserts a facecard bearing the subject signature into a data reader 64. The signature on the data acts as a reference for comparison with a new signature which is generated through the same steps 34–48 as described above in connection with FIG. 2.

Following feature extraction at step 48, correlation analysis 66 is performed to compare the reference data image from the card with the data derived from the contemporaneously generated image.

Figure 8:
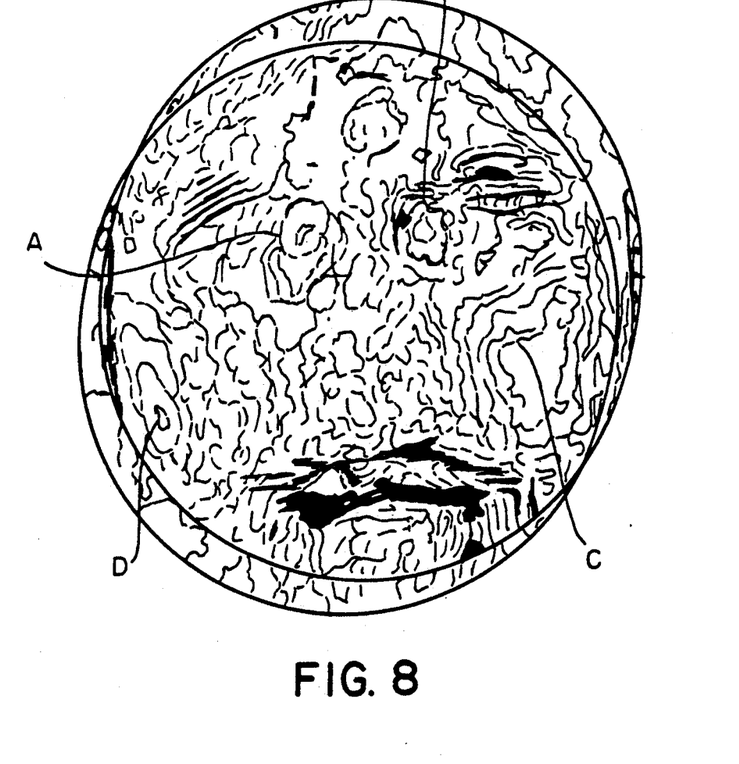
FIG. 8 illustrates correlation of two images to identify a match of certain features thereof.

More particularly, for statistical analysis a cross correlation is performed in which an elemental shape of the reference faceball is correlated across an area of the currently presented faceball. This correlation is represented in FIG. 8 with respect to the elemental shape B. The area is set to enclose all possible transpositions of that thermal feature which could be due to twisting, tilting or tipping of either faceball relative to the other or to variations in the imaging sensor.

A detailed representation of elemental shape B is shown in FIG. 9. The feature area is bounded by minimum and maximum values of coordinates a and b. The correlation matrix C (x, y) is derived from $$\sum_{a=a_{min}}^{a_{max}} \sum_{b=b_{min}}^{b_{max}} |R(a, b) - U(a - x, b - y)|$$

where
R(a, b) is the reference faceball.
U(a, b) is the unknown current faceball.

If the resulting cross correlation matrix contains a global minimum, that minimum is compared to a predetermined threshold value representing a required quality of fit for recognition 68.

Figure 10:
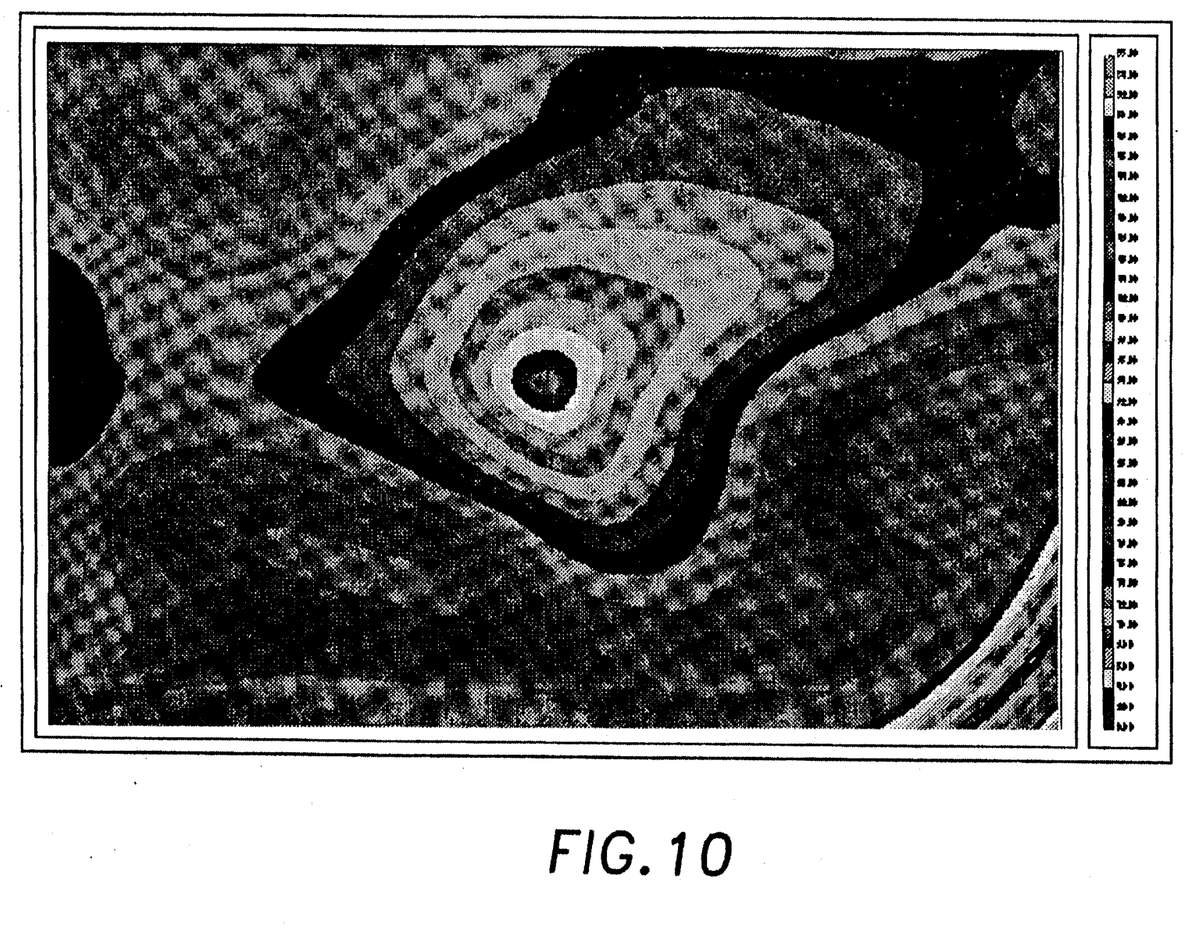
FIGS. 10 and 11 illustrates the correlation results of good and bad match areas, respectively.

If the global minimum is below the threshold, the current faceball is recognized as being the same as the reference 70 and admission to the secure area is afforded 72. An entry report is made 74 and the system returns to its idle state 76. A good match is shown in FIG. 10.

If the global minimum is above the threshold, then other local minimums are evaluated. If the cross correlation matrix contains more than one local minimum, then each minimum is examined in order starting at the center of the matrix and proceeding outwardly. A local minimum is considered of valid interest if it is the center of a number of concentric contours of increasing value. The tightness and number of the concentric contours is computed, i.e. the number of concentric rings occuring about the local minimum within the matrix. In cases where the local minimum occurs near the edge of the cross correlation matrix, incompleted rings are counted as if they were completed. A local minimum which does not have at least the minimum number of rings (set to two or more) is discarded, and the next minimum is considered. If a local minimum has at least the minimum number of rings, then it is compared to the threshold. If it is less, then the current faceball is recognized as being the reference or known person.

Figure 11:
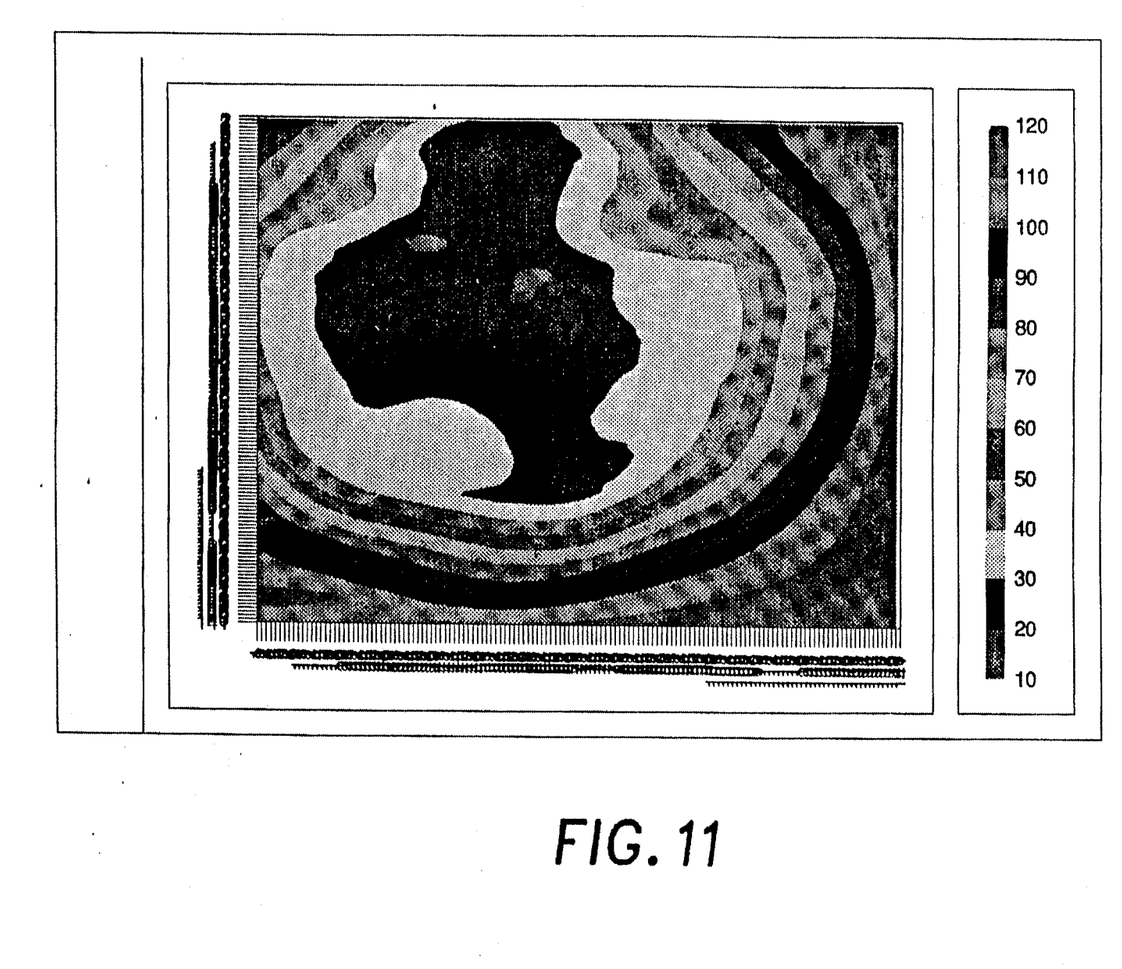

If too many comparisons are performed in which the global minimum is above the threshold 78, the system determines that the individual does not correspond with the reference from the identification card. A bad match is shown in FIG. 11. A purge sequence is initiated 80, an entry denial report is issued 82, and the system returns to the idle state without granting access to the individual.

Rather than compare a current thermal image with one entered via an identification card, comparison may be made with a number of known faceballs stored in the system memory and corresponding with thermal images of authorized individuals.

If no global minimum is located which meets the threshold test of a first stored faceball, the unknown or currently generated faceball is matched against the next known faceball in the memory.

If additional security is required, several elemental shapes may be compared between known and unknown faces, before recognition is claimed. In the case comparing a presented face to the face represented on an identification card, one such pass through the comparison algorithm yields the required match/no match decision. In the case where a presented face is to be matched against a data base of known facts, it will speed the search if the data base is arranged according to similarly shaped elementary contours.

The elemental shapes may be considered in using a fractal representation of the known or unknown faces. If the database includes fractal-compressed face signatures, then the search may compare first the elemental shapes, and then the fractal-encoded patterns, rather than requiring each candidate known face to be first decompressed prior to correlation.

The threshold is set, for a particular hardware embodiment and application, in any adaptive manner such that it recognizes known faces and when they have a reasonable amount of inconsistency in position and orientation, and in face and ambient temperature ranges and yet does not mismatch unknown faces to similar known faces.

For geometric analysis, a faceball signature is read from a card that the individual inserts into a card reader. The data from the card is used as a reference for comparison to the newly acquired data. Alternatively, the reference signature may be accessed from a centralized data base by use of keyboard command, voice command, or other types of identifiers. The retrieved file is then appended to the faceball data file. The faceball area of search is defined by the location of the centroid of the extracted original faceball shape a predetermined percentage of the largest dimension both horizontally and vertically. The results of the comparison are then mapped to a separate results file. A shape vector map and pixel location of the centroid are saved in the file.

The resultant vector map and centroid are compared to the original signature file and the results are recorded. These results are then compared to a predetermined set of threshold data used to determine the probability of match. Each feature is analyzed individually based on a ranking order and a decision to compare additional features is made based on the previous result. A single pass fail result is then issued.

Finally, for fractal analysis, the original signature file is either read from a card that the individual is carrying or the file may be accessed from a central data base by use of keyboard command, a voice command or other types of identifier. The retrieved file is then appended to the faceball data file. For fractal analysis, the faceball area of search is defined by the location of the extracted fractal in the original faceball to a predetermined percent of the expanded fractal shape in both vertical and horizontal dimensions. The results of the search and comparison are then mapped to a separate results file.

The resultant fit data and location of closest match are compared to the original signature file and the results are recorded. These results are then compared to a predetermined set of threshold data used to determine the probability of match. Each feature is analyzed individually based on a ranking order and a decision to compare additional features is made based on the previous result. A single pass fail result is then issued.

There has been described and illustrated herein a fully secure apparatus and method for positively and uniquely identifying an individual, and a security system utilizing the identification apparatus and method. While particular embodiments of the invention have been described, it is not intended that the invention be limited thereby, as it is intended that the invention be broad in scope and the specifications be read likewise. Thus, while a preferred algorithm for identification has been described, the algorithm may be changed and refined in many ways. Moreover, the criteria for determining that a "match" has been found may be set according to various requirements. Thus, depending on the level of security desired, the storage capacity of the card, and the accuracy of the system provided, a match may be determined to have been found if one or more elemental shape is similar.

While particular elemental shapes and quality of fit criteria were described as being preferred for determining an individual's identity, those skillet in the art will recognize that depending upon the desired accuracy of the system, fewer or more parameters, as well as different parameters could be utilized. Likewise, while discussion was had with regard to obtaining facial image information from a frontal view with a scanning thermal imager sensitive in the 3 to 6 micron range, it will be appreciated that information could also be gleaned from other types of thermal imagers, at other wavelengths, as well as from other types of biosensors whose output an be represented as n-dimensional images. Indeed the techniques of the invention can be used to identify animals or abnormalities in the body such as migraine headaches, inflammation, arthritis, arterial blockages, or the presence of false facial hair.

While particular biosensor data has been described, those skilled in the art will recognize that depending upon the desired accuracy of the system, fewer or more biosensors, as well as different biosensor data presentations could be utilized. Also, while the storing of reference sensor data is preferably in the form of grey scale recordings of 8 bit data from an array of at least $256 \times 240$ pixels, indications of values may be obtained and stored in many ways. For example, the information storage means on the identification card could range, e.g., from a laminated magnetic strip, to an embedded integrated circuit, to encoding by laser deformation on a metallic card.

Further yet, it will be appreciated that the computing equipment could vary greatly, as different types of computers and data entry devices could be used. Various techniques could also be employed for arranging that the face to be identified is aligned with the imaging biosensor, and various correlation techniques can be employed for searching a data file for the best match or comparing images resulting from a presented card and from its holder. Therefore, it will be apparent to those skilled in the art that many other changes and modifications may be made to the invention as described in the specification without departing from the spirit and scope of the invention as so claimed.

What is claimed:

1. A method for identifying individuals from biosensor data, comprising the steps of
   (a) generating a thermal image of a portion of an individual's body in accordance with the thermal energy patterns thereof;
   (b) processing said thermal image to produce a digital representation thereof, said digital representation comprising a matrix of pixels, the intensity of each pixel corresponding with the level of thermal energy of a corresponding portion of said image;
   (c) normalizing said image in order to eliminate variables therefrom, thereby to produce an image containing elemental shapes comprising contours corresponding with unique structural features of the individual; and
   (d) storing said normalized digital representation of said image, whereby a unique digital representation is created and stored for every individual for subsequent identification.

2. A method as defined in claim 1, wherein said normalizing step includes cropping said image to an area of minimum thermal variation over time and maximum uniqueness.

3. A method as defined in claim 2, wherein said cropped image area comprises a portion of the individual's face containing the eyes and nose.

4. A method as defined in claim 2, wherein said cropping step is performed by
   (1) detecting the edges of said image;
   (2) defining vertical and horizontal axes of said image with respect to intensity levels thereof; and
   (3) deleting excess portions of said image.

5. A method as defined in claim 2, wherein said normalizing step further includes the step of standardizing said image for size by measuring a field of interest and scaling said field to preserve and reconstruct said image to a standard size.

6. A method as defined in claim 5, wherein said normalizing step further includes the step of equalizing said image to a standard histogram in accordance with specific feature areas of said image.

7. A method as defined in claim 1, and further comprising the step of identifying regions of said image containing elemental shapes of interest.

8. A method as defined in claim 7, and further comprising the step of storing at least a portion of each region containing an elemental shape with respect to its location on the image in a memory.

9. A method as defined in claim 8, wherein each of said regions is defined by one of geometry, mathematics, and as a bit-map replica of said region, thereby to provide a signature of the individual.

10. A method as defined in claim 9, and further comprising the step of comparing a previously defined reference signature of an individual with a currently defined signature of the individual to confirm the individual's identity.

11. A method as defined in claim 10, wherein said comparison step is accomplished using correlation techniques.

12. A method as defined in claim 10, wherein said comparison step comprises matching the location and configuration of each of said elemental shapes.

13. A method as defined in claim 12, and further comprising the step of adaptively establishing a threshold level of match to confirm the individual's identity, whereby the threshold level must be met in order to confirm the individual's identity.

14. A method as defined in claim 13, wherein said portion of the individual's body comprises the face, and further wherein said normalized image contains elemental shapes corresponding with at least the eyes and nose of the individual.

* * * * *